United States Patent [19]

Kim et al.

[11] Patent Number: 5,401,641
[45] Date of Patent: Mar. 28, 1995

[54] PRODUCTION OF ANTIBODY CATALYSTS

[75] Inventors: Peter S. Kim, Brookline, Mass.;
Neville R. Kallenbach, New York, N.Y.

[73] Assignee: IGEN, Inc, Rockville, Md.

[21] Appl. No.: 73,285

[22] Filed: Jun. 7, 1993

Related U.S. Application Data

[60] Continuation of Ser. No. 564,882, Aug. 9, 1990, abandoned, which is a division of Ser. No. 64,239, Jun. 19, 1987, Pat. No. 4,963,355, which is a continuation-in-part of Ser. No. 877,273, Jun. 23, 1986, Pat. No. 4,792,446.

[51] Int. Cl.$^6$ ............................ C12P 1/00; C12N 9/00
[52] U.S. Cl. ............................ 435/41; 435/188.5; 530/388.9; 530/389.8
[58] Field of Search ...................... 435/188.5, 183, 41, 435/240.27

[56] References Cited

U.S. PATENT DOCUMENTS 4,888,281 12/1989 Schochetman et al. .............. 435/72
4,963,355 10/1990 Kim et al. ......................... 424/85.8

OTHER PUBLICATIONS

Ashley, J. A., et al. (1993) J. Am. Chem. Soc. 115, 2515–2516.
Janda, K. D. et al. (1991) J. Am. Chem. Soc. 113, 5427–5434.
Iverson, B. L., et al. (1989) Science 243, 1184–1188.
Janda, K. D., et al., (1990) J. Am. Chem. Soc. 112, 1274–1275.
Shokat, K. M., et al. (1989) Nature 338, 269–271.
Erhan and Greller, *Nature,* vol. 251, p. 353 (1974).

*Primary Examiner*—Charles L. Patterson, Jr.
*Attorney, Agent, or Firm*—Curtis Morris & Safford; Barry Evans

[57] ABSTRACT

Process for producing an antibody catalyst for a chemical reaction. Chemical reactions in which the antibody catalyst can be used are also disclosed.

24 Claims, No Drawings

PRODUCTION OF ANTIBODY CATALYSTS

This application is a continuation of application Ser. No. 07/564,882, filed Aug. 9, 1990, now abandoned, which is a divisional of application Ser. No. 07/064,239, filed Jun. 19, 1987, now U.S. Pat. No. 4,963,355, which is a continuation-in-part of application Ser. No. 06/877,273, filed Jun. 23, 1986, now U.S. Pat. No. 4,792,446.

BACKGROUND OF THE INVENTION

1. Field of the Invention

This invention involves novel antibody catalysts and a process for their production. The process includes selecting a hapten based on its relationship to the structure and reactivity of a selected substrate so that the hapten, upon attachment to a carrier protein and injection into an animal, elicits an immune response in which the desired antibody is produced.

There has been a long felt, and there is at present, an increasing need for more specific or selective catalysts capable of accelerating rates of desired chemical reactions. Catalysts are used widely in the chemical, pharmaceutical and food processing industries to improve normally unfavorable reaction rates. Among known catalysts, enzymes—naturally occurring protein molecules—excel in terms of their ability to select one reactant species among a large excess of others and to generate the highest acceleration of reaction rates concomitant with this selectivity. Simpler catalysts—based on organics or metals, for instance—lack the ability of enzymes to select substrates. The success of enzymes is attributed to the ability of proteins to fold spatially so as to create specific pockets for binding a reactant, and to place catalytically active groups within these pockets in proximity to a reactant. These pockets are referred to as "active sites".

A major obstacle to creating new enzymes which would operate upon a predetermined reactant and selectively catalyze a desired chemical transformation on this species is the understanding of how proteins achieve their spatial folded form. Minor alterations to an enzyme (and its function as a catalyst) are possible, via site-directed alterations in its sequence. However, substitution of a single amino acid for another in the sequence of a protein can affect the conformation and/or function of the molecule in a severe and unpredictable manner.

2. Description of the Prior Art

International Patent PCT/US84/01951; Lerner (Advances in Immunology 36, 1, 1984); Raso and Stollar (Biochemistry 14, 585, 591, 1975); Kohen et al (FEBS Letters 100, 137, 1979; 104, 201, 1979; 111, 427, 1980; and Biochim. Biophys. Acta. 629, 328, 1980); Slobin (Biochemistry 5, 2836, 1966); and G. P. Royer (Advances in Catalysis, 29, 197–227, 1980) are cited as representative of the state of the art.

SUMMARY OF THE INVENTION

The present invention comprises a process for producing an antibody catalyst for a chemical reaction which comprises identifying a substrate for said reaction, selecting a hapten which is corresponding to said substrate, stimulating an immune response by said hapten for production of antibodies which are catalytically active for said chemical reaction and isolating said antibodies from said immune response which are catalytically active for said chemical reaction.

DESCRIPTION OF THE SPECIFIC EMBODIMENTS

The present invention comprises novel antibody catalysts and a process for their production. The antibody catalysts of the present invention are capable of acting in vitro as well as in vivo, and in the human body itself. The catalysts of this invention are antibody molecules, obtained by an immunization with a hapten that is related to, but distinct from, the selected substrate of the reaction to be catalyzed. This relationship is the following: at least one chemical group in the hapten is identical in both its structure and orientation with a group in the substrate. This insures that the hapten and substrate share antigenic determinants; i.e., the binding site of the antibody catalyst stimulated by hapten must interact with substrate; the hapten must also differ structurally and chemically from the substrate in the vicinity of the nuclei and associated bonds to be altered in the reaction, e.g., one or more nuclei of higher valence in the hapten is substituted for the nucleus or nuclei in the substrate; further, the substituted nucleus or nuclei bear substituents, the role of which is to position complementary, catalytic groups within the antibody binding surface and to create an additional cavity or cavities capable of enclosing cofactor molecules. The presence of one or more substantially similar groups or residues ensures that the hapten and substrate share common antigenic determinants. This in turn, ensures that the antibody catalyst will "recognize" the substrate in a selective manner. On the other hand, the hapten differs structurally and chemically from the substrate in the vicinity of the bond (or bonds) to be altered in the reaction. Differences include substituting a nucleus of higher valency for one or more such nuclei in the substrate. In addition, residues in the antigen appended from these nuclei are so oriented that they complement antibody groups that promote catalysis. The presence of catalytic groups in the antibody binding surface endows these antibodies with catalytic power in addition to their normal and highly selective binding capacity. The antibody catalysts of the process, whether obtained polyclonally or monoclonally, are well-folded, stable proteins by virtue of their derivation in an immune response. This invention thus circumvents present uncertainties concerning folding of proteins of novel sequence. The process of immunization using the haptens of this invention to produce antibody catalysts is defined as active immunization.

The proteins of this invention thus include a novel class of antibodies that are chemically reactive against their target antigenic species, in that they catalyze cleavage of bonds in these targets in the manner that a hydrolytic enzyme does, instead of passively binding antigens.

A large class of chemical reactions that can be catalyzed by antibodies are general acid-base interactions between catalyst and substrate in the transition state. Hydrolytic reactions are included in this class. Significant increase in rates of these reactions occurs on approximation of the appropriate chemical groups with little specific orientation. A second class of applicable reactions (including fragmentation processes such as decarboxylation) proceeds via stabilization or destabilization of charges. Again precise orientation of these groups is not required.

Definitions

Substrate—the reactant molecule to be converted chemically in a particular chemical transformation to product.

Cofactor—additional molecule(s) participating in the reaction, including $H_2O$ in hydrolytic reactions.

Hapten—a molecule attached covalently to a carrier protein that elicits an antibody response directed towards itself.

Antigen—the combined hapten-carrier complex used to stimulate the immune response.

The selected substrate is represented as a tripartite molecule $$R_1 - X - R_2 \qquad \text{FORMULA I}$$

wherein $R_1$ and $R_2$ which do not participate in the catalytic events represent the residual chemical groups in the substrate after the catalytically active nuclei has been designated as X. X represents nuclei and associated bonds to be altered in the catalytic reaction, i.e., the reaction site.

The haptens of this invention corresponding to the substrate are molecules selected, or synthesized chemically, having the structure, $$\overset{\overset{\displaystyle Q}{|}}{R_1' - Y - R_2'} \qquad \text{FORMULA II}$$

wherein $R_1'$ and $R_2'$ are substantially similar to $R_1$ and $R_2$ of the substrate (except for possible addition of a group linking the hapten to a carrier) and Y represents nuclei and associated bonds which comprise the catalytically active portion of the hapten molecule, and:

(1) X and Y are related to each other in that Y has a higher valence state and one or more bonds than X. Table 2 represents this relationship between X and Y.

(2) Q represents one (or more) substituents bonded to Y in (1) such that:

(a) Q contains a negative charge(s) when the catalysis requires a positive charge(s) in the active surface of the antibody catalyst, and vice-versa.

(b) Q is polar or neutral when catalysis requires a polar component of said active surface.

(c) Q is non-polar (or hydrophobic) when catalysis requires a non-polar component in said active surface.

(d) When one or more cofactors are involved in the reaction, Q is selected to be a substituent of substantial bulk so as to create a cavity in the active surface to allow for one or more of said co-factors to bind, including $H_2O$ in the case of hydrolytic reaction.

(e) Q can contain in addition a group capable of linking the hapten to carrier, in case attachment at the Y region is desired.

When several possible substituents are appropriate for the catalytic process of this invention, preferred choices are selected as those which minimize differences in binding affinity between the substrate and the hapten. These affinities are tabulated in the treatise by Pressman and Grossberg, The Structural Basis of Antibody Specificity, Benjamin, N.Y. 1969, for example. These data are used to ensure a sufficient degree of similarity in binding of substrate and hapten such that both molecules will be bound by the antibody catalysts resulting from this invention.

(3) the remaining groups $R_1'$ and $R_2'$ comprising Y are selected to be identical to or of similar size and charge to corresponding groups in X, i.e., they are substantially similar.

The Formulas I and II and the algorithm set forth above defines the correspondence between the hapten and substrate in this invention, i.e., hapten is selected or synthesized to correspond to the substrate according to above Formulas I and II.

Identity of X in important substrates that comprise the bond(s) altered in hydrolytic reactions:

TABLE 1

| Reaction | Substrate | X |
|---|---|---|
| General ester hydrolysis | $R_1-\overset{\overset{\displaystyle O}{\|}}{C}-O-R_2 + H_2O \longrightarrow$ | $-\overset{\overset{\displaystyle O}{\|}}{C}-O-$ |
| | $R_1-\overset{\overset{\displaystyle O}{\|}}{C}-OH + HO-R_2$ | |
| General amide hydrolysis | $R_1-\overset{\overset{\displaystyle O}{\|}}{C}-NH-R_2 + H_2O \longrightarrow$ | $-\overset{\overset{\displaystyle O}{\|}}{C}-NH-$ |
| | $R_1-\overset{\overset{\displaystyle O}{\|}}{C}-OH + H_2N-R_2$ | |
| General phosphodiester hydrolysis | $R_1-O-\overset{\overset{\displaystyle O}{\|}}{\underset{\underset{\displaystyle O(-)}{\|}}{P}}-O-\overset{\overset{\displaystyle R_2}{\|}}{\underset{\underset{\displaystyle R_2}{\|}}{C}}-R_2 + H_2O \longrightarrow$ | $-\overset{\overset{\displaystyle O}{\|}}{P}-O-\overset{\overset{\displaystyle \|}{\|}}{C}-$ |
| | $R_1-O-\overset{\overset{\displaystyle O}{\|}}{\underset{\underset{\displaystyle O(-)}{\|}}{P}}-OH + HO-\overset{\overset{\displaystyle R_2}{\|}}{\underset{\underset{\displaystyle R_2}{\|}}{C}}-R_2$ | |

TABLE 1-continued

| Reaction | Substrate | X |
|---|---|---|
| General heterolytic fragmentation | $W^* - \underset{\underset{R_2}{\vert}}{\overset{\overset{R_1}{\vert}}{C}} - \underset{\vert}{\overset{\vert}{C}} - \underset{\vert}{\overset{\vert}{C}} - Z^* \longrightarrow$ $(+)W = C\overset{R_1}{\underset{R_2}{\diagdown}} \quad + \quad \diagdown C = C \diagup \quad + \quad Z^{(-)}$ | $W - \underset{\vert}{\overset{\vert}{C}} - \underset{\vert}{\overset{\vert}{C}} - \underset{\vert}{\overset{\vert}{C}} - Z$ |
| General acetal hydrolysis | $R_1 O - \underset{\underset{R_1}{\vert}}{\overset{\overset{R_2}{\vert}}{C}} - O - R_2 + H_2 O \longrightarrow$ $R_1 O - \underset{\underset{R_1}{\vert}}{\overset{\overset{R_2}{\vert}}{C}} - OH + HOR_2$ | $-\underset{\vert}{\overset{\vert}{C}} - O-$ |

*W represents electron donating group, *Z represents electron withdrawing group.

TABLE 2

Substitutions of Higher Valence For Nuclei In the X Region Of The Reactant

| Substrate: Nuclei in X | Hapten: Nuclei in Y |
|---|---|
| O,S (oxygen, sulfur) | N or C (nitrogen or carbon) |
| N (nitrogen) | C (carbon) |
| C (carbon) | P (phosphorus) |

Identity of X, $R_1$ and $R_2$ of substrate in the following hydrolysis reaction:

TABLE 3

| Substrate (uric acid) | X | $R_1$ | $R_2$ |
|---|---|---|---|

Identity of Y, $R_1'$ and $R_2'$ of haptens that correspond to substrate in the hydrolysis reaction above:

TABLE 4

| | Y | $R_1'$ | $R_2'$ |
|---|---|---|---|
| Hapten | | | |
| (Example 1 infra) | | | |

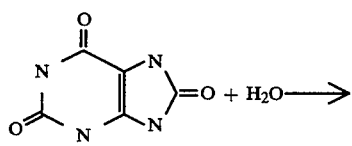

Identify of X, $R_1$ and $R_2$ of substrate in following decarboxylation reaction:

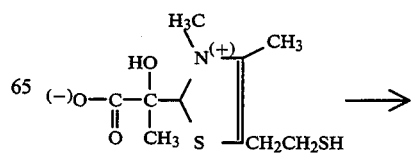

-continued

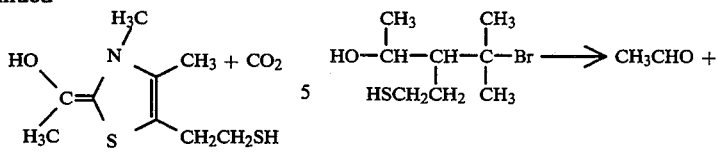

TABLE 5

| Substrate (Example 3 infra) | X | $R_1$ | $R_2$ |
|---|---|---|---|
| [structure with N(±), HO, (−)O−C−C(=O)−CH₃, CH₃, S, CH₂CH₂SH] | [structure with N, HO, (−)O−C−C(=O)−CH₃, CH₃, S] | −CH₃ | −CH₂CH₂SH |

Identity of Y, $R_1'$ and $R_2'$ of haptens that correspond to substrate in above decarboxylation reaction:

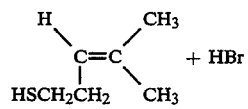

TABLE 6

| Hapten (Example 2 infra) | Y | $R_1'$ | $R_2'$ |
|---|---|---|---|
| [H₂N−C(=O)−C(CH₃)(OH)−C(CH₃)=C(S−)(CH₂CH₂SH)] | [H₂N−C(=O)−C(CH₃)(OH)−C(CH₃)=C(S−)−] | −CH₃ | −CH₂CH₂SH |
| [H₃C−C(=O)−C(CH₃)(OH)−C(CH₃)=C(S−)(CH₂CH₂SH)] | [H₃C−C(=O)−C(CH₃)(OH)−C(CH₃)=C(S−)−] | −CH₃ | −CH₂CH₂SH |
| [H₃CO−C(=O)−C(CH₃)(OH)−C(CH₃)=C(S−)(CH₂CH₂SH)] | [H₃CO−C(=O)−C(CH₃)(OH)−C(CH₃)=C(S−)−] | −CH₃ | −CH₂CH₂SH |
| [H₂N−P(=O)(CH₃)−C(CH₃)=C(S−)(CH₂CH₂SH) with H₃C] | [H₂N−P(=O)(CH₃)−C(CH₃)=C(S−)− with H₃C] | −CH₃ | −CH₂CH₂SH |

Identity of X, $R_1$, and $R_2$ of substrate in the following heterolytic fragmentation reaction:

TABLE 7

| Substrate (Example 5 infra) | X | $R_1$ | $R_2$ |
|---|---|---|---|
| HO−CH(CH₃)−CH(HSCH₂CH₂)−C(CH₃)(CH₃)−Br | HO−CH(CH₃)−CH−C(CH₃)(CH₃)−Br | −CH₃ | −CH₂CH₂SH |

Identity of Y, $R_1'$, $R_2'$ of a hapten that corresponds to substrate in the fragmentation reaction above:

TABLE 8

| Hapten (Example 4 infra) | Y | $R_1'$ | $R_2$ |
|---|---|---|---|
| H₂N−CH(CH₃)−CH(HSCH₂CH₂)−C(CH₃)−CO₂H | H₂N−CH(CH₃)−CH−C(CH₃)−CO₂H | −CH₃ | −CH₂CH₂SH |

Identity of X, $R_1$ and $R_2$ in the following hydrolytic reaction:

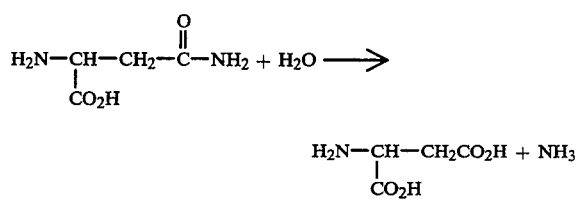

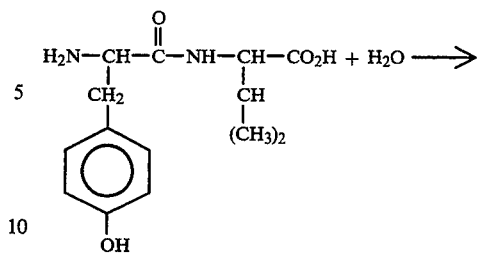

TABLE 9

| Substrate (asparagine) | X | $R_1$ | $R_2$ |
|---|---|---|---|
| $H_2N-CH-CH_2-\overset{O}{\underset{\|}{C}}-NH_2 + H_2O$<br>$\|$<br>$CO_2H$ | $-\overset{O}{\underset{\|}{C}}-NH-$ | $-CO_2H$ | $H_2N-CH-CH_2$<br>$\|$ |

Identity of Y, $R_1'$, and $R_2'$ of a hapten which corresponds to the substrate in the reaction above:

TABLE 10

| Hapten | Y | $R_1'$ | $R_2'$ |
|---|---|---|---|
| 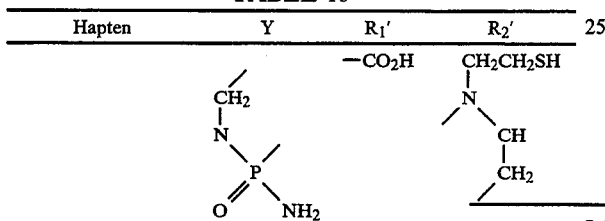 | 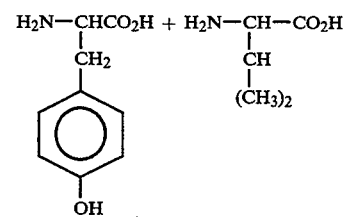 | $-CO_2H$ | $CH_2CH_2SH$<br>$\|$<br>$N$<br>$/ \ $<br>$CH$<br>$\|$<br>$CH_2$ |

Identity of Y, $R_1'$ and $R_2'$ of a hapten which corresponds to the substrate in the reaction above:

TABLE 11

| Substrate | X | $R_1$ | $R_2$ |
|---|---|---|---|
| $H_2N-CH-\overset{O}{\underset{\|}{C}}-NH-CH-CO_2H$<br>$\|$ $\qquad$ $\|$<br>$CH_2$ $\qquad$ $CH$<br>$\|$ $\qquad\quad$ $\|$<br>(ring-OH) $\;$ $(CH_3)_2$ | $-\overset{O}{\underset{\|}{C}}-NH-$ | $H_2N-CH-$<br>$\|$<br>$CH_2$<br>$\|$<br>(ring-OH) | $-CH-CO_2H$<br>$\|$<br>$CH$<br>$\|$<br>$(CH_3)_2$ |

TABLE 12

| Hapten | Y | $R_1'$ | $R_2'$ |
|---|---|---|---|
| $H_2N-CH-\overset{O}{\underset{\|}{P}}-CH-CH-NH-\overset{O}{\underset{\|}{C}}CH_2-NH_2$<br>$\|$ $\quad\;$ $\|$ $\qquad$ $\|$<br>$CH_2$ $\;$ $NH_2$ $\qquad$ $CH$<br>$\|$ $\qquad\qquad\qquad\;\;$ $\|$<br>(ring-OH) $\qquad\qquad\;$ $(CH_3)_2$ | $-\overset{O}{\underset{\|}{P}}-\overset{CO_2H}{\underset{\|}{CH}}-$<br>$\|$<br>$NH_2$ | $H_2N-CH-$<br>$\|$<br>$CH_2$<br>$\|$<br>(ring-OH) | $-\overset{O}{\underset{\|}{\;}}$<br>$-CH-NH-\overset{\|}{C}-CH_2NH_2$<br>$\|$<br>$CH$<br>$\|$<br>$(CH_3)_2$ |

Identity of X, $R_1$ and $R_2$ in the following deblocking reaction:

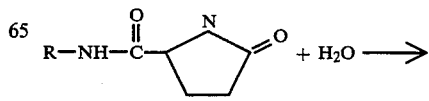

Identity of X, $R_1$, and $R_2$ in the following hydrolytic reaction:

-continued

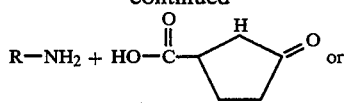

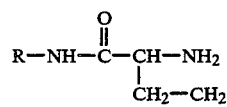

R = remainder of the peptide chain

Identity of X, $R_1$, and $R_2$ in the following deprotecting reaction:

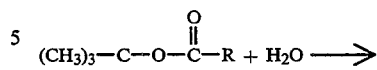

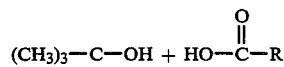

R = the remainder of the protected organic acid

TABLE 15

| Substrate | X | $R_1$ | $R_2$ |
|---|---|---|---|
| $(CH_3)_3-C-O-\overset{O}{\underset{\|}{C}}-CH_2-\overset{CH_3}{\underset{\underset{CH_3}{\|}}{C}}-CO_2H$ | $-O-\overset{O}{\underset{\|}{C}}-$ | $(CH_3)_3-\overset{O}{\underset{\|}{C}}-$ | $-CH_2-\overset{CH_3}{\underset{\underset{CH_3}{\|}}{C}}-CO_2H$ |
|  | or |  |  |
|  | $-\overset{O}{\underset{\|}{C}}-O-$ | $(CH_3)_3-$ | $-\overset{O}{\underset{\|}{C}}-CH_2-\overset{CH_3}{\underset{\underset{CH_3}{\|}}{C}}-CO_2H$ |

TABLE 13

| Substrate | X | $R_1$ | $R_2$ |
|---|---|---|---|
| $R-NH-\overset{O}{\underset{\|}{C}}-\underset{\text{(cyclopentanone ring)}}{}=O$ | $-NH-\overset{O}{\underset{\|}{C}}-$ | $-R$ | $\underset{\text{(pyrrolidinone)}}{N=O}$ |
|  |  | or | or |
|  |  | $R-NH-\overset{O}{\underset{\|}{C}}-$ | $-CH_2 \underset{CH_2-CH_2}{\diagdown}$ |

Identity of Y, $R_1'$, and $R_2'$ of two haptens—one corresponding to each pathway—corresponding to substrate in the reaction above:

Identity of Y, $R_1'$, and $R_2'$ of two haptens which correspond to the substrate in the reaction above (one for each X):

TABLE 14

| Hapten | Y | $R_1'$ | $R_2'$ |
|---|---|---|---|
| $HS-CH_2CH_2-\underset{HO_2C}{\underset{\|}{CH}}-\underset{NH_2}{\overset{O}{\underset{\|}{P}}}-\underset{\text{(pyrrolidinone)}}{}=O$ | $-\underset{HO_2C}{\underset{\|}{CH}}-\underset{NH_2}{\overset{O}{\underset{\|}{P}}}-$ | $HS-CH_2CH_2-$ | $\underset{\text{(pyrrolidinone)}}{N=O}$ |
| $HS-CH_2CH_2-NH-\overset{O}{\underset{\|}{C}}-\underset{\text{(ring with } CO_2H)}{}\overset{O}{\underset{\|}{P}}-NH_2$ | $\underset{\overset{\|}{O=P-NH_2}}{\underset{\|}{CH}-CO_2H}$ (isopropyl) | $HS-CH_2CH_2-NH-\overset{O}{\underset{\|}{C}}-$ | $-\underset{CH_2}{\underset{\|}{CH_2}}\underset{\|}{CH_2}$ |

TABLE 16

| Hapten | Y | $R_1'$ | $R_2'$ |
|---|---|---|---|
| $(CH_3)_3-\underset{HO_2C}{\underset{\|}{C}}-\underset{NH_2}{\underset{\|}{C}}H-\overset{O}{\underset{\|}{P}}-CH_2-\overset{CH_3}{\underset{\underset{(CH_2)_3SH}{\|}}{C}}-CO_2H$ | $-\underset{HO_2C}{\underset{\|}{C}}H-\underset{NH_2}{\overset{O}{\underset{\|}{P}}}-$ | $(CH_3)_3-C-$ | $-CH_2-\overset{CH_3}{\underset{\underset{(CH_2)_3-SH}{\|}}{C}}-CO_2H$ |

TABLE 16-continued

| Hapten | Y | $R_1'$ | $R_2'$ |
|---|---|---|---|
| $(CH_3)_3-C-\underset{CO_2H}{\overset{H}{\underset{|}{C}}}-\overset{O}{\overset{\|}{C}}-CH_2-\underset{(CH_2)_3-SH}{\overset{CH_3}{\underset{|}{C}}}-CO_2H$ | $-\underset{CO_2H}{\overset{H}{\underset{|}{C}}}-\overset{}{\underset{|}{C}}-$ | $(CH_3)_3-$ | $-\overset{O}{\overset{\|}{C}}-\underset{(CH_2)_3-SH}{\overset{CH_3}{\underset{|}{C}}}-CO_2H$ |

Identity of X, $R_1$, and $R_2$ in the following acetal protecting group removal:

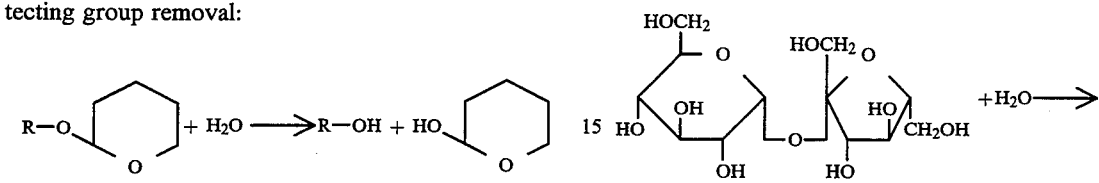

R = the remainder of the protected alcohol.

TABLE 17

| Substrate | X | $R_1$ | $R_2$ |
|---|---|---|---|
| H₂N—CH₂—CH—OH (with phenyl-O-tetrahydropyran substituent) | —O—C— | H₂N—CH₂—CH—OH (with p-methylphenyl) | tetrahydropyran |

Identity of Y, $R_1'$, and $R_2'$ of a hapten which corresponds to the substrate in the reaction above:

TABLE 18

| Hapten | Y | $R_1'$ | $R_2'$ |
|---|---|---|---|
| H₂N—CH₂—CH—OH with (CH₂)₃SH and phenyl bearing HO₂C—N, H₂N, tetrahydropyran | $-\underset{NH_2}{\overset{CO_2H}{\underset{|}{N-C-}}}$ | H₂N—CH—CH—OH with (CH₂)₂SH and p-methylphenyl | tetrahydropyran |

Identity of X, $R_1$, and $R_2$ in a sucrose hydrolysis:

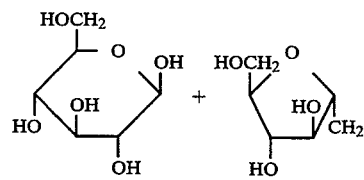

TABLE 19

| Substrate (sucrose) | X | $R_1$ | $R_2$ |
|---|---|---|---|
| (sucrose structure) | —C—O— | (glucose moiety) | (fructose moiety) |

Identity of Y, $R_1'$, and $R_2'$ in a hapten which corresponds to the substrate in the reaction above:

TABLE 20

| Hapten | Y | R₁' | R₂' |
|---|---|---|---|

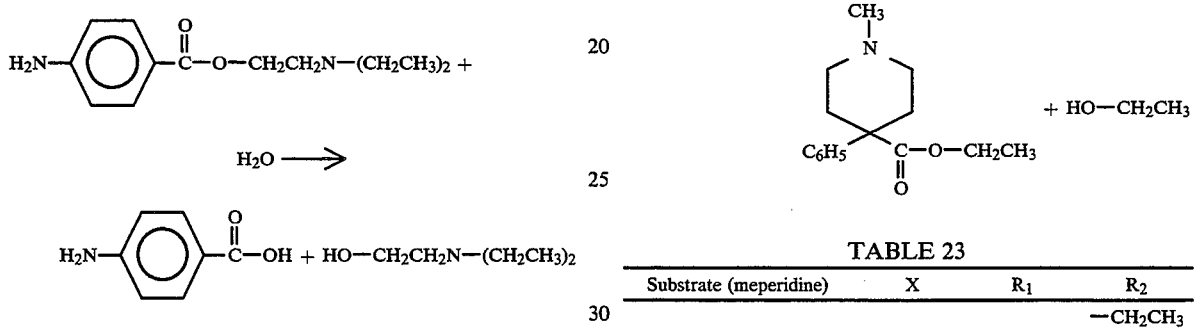

Identity of X, R₁ and R₂ in procaine hydrolysis:

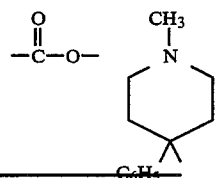

TABLE 21

| Substrate (procaine) | X | R₁ | R₂ |
|---|---|---|---|

Identity of Y, R₁', and R₂' on a hapten which corresponds to the substrate in the reaction above:

TABLE 22

| Hapten | Y | R₁' | R₂' |
|---|---|---|---|

Identity of X, R₁ and R₂ in meperidine hydrolysis:

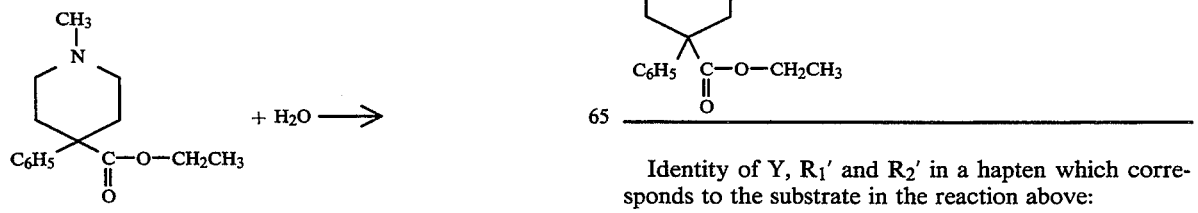

TABLE 23

| Substrate (meperidine) | X | R₁ | R₂ |
|---|---|---|---|
|  |  |  | —CH₂CH₃ |

Identity of Y, R₁' and R₂' in a hapten which corresponds to the substrate in the reaction above:

TABLE 24

| Hapten | Y | R₁' | R₂' |
|---|---|---|---|
| (structure with SH-(CH₂)₂-N-piperidine with C₆H₅ and P(=O)(NH₂)-CH(CO₂H)-CH₂CH₃) | -P(=O)(NH₂)-CH(CO₂H)- | (structure with SH-(CH₂)₂-N-piperidine with C₆H₅) | -CH₂CH₃ |

Identity of X, R₁, and R₂ in the hydrolytic breakdown of lidocaine:

Identity of Y, R₁' and R₂' in a hapten which corresponds to the substrate in the reaction above:

TABLE 26

| Hapten | Y | R₁' | R₂' |
|---|---|---|---|
| HS—(CH₂)₂—(2,6-dimethylphenyl with HO₂C)—CH—P(=O)(NH₂)—CH₂N—(CH₂CH₃)₂ | -CH(HO₂C)-P(=O)(NH₂)- | HS—(CH₂)—(2,6-dimethylphenyl) | -CH₂N(CH₂CH₃)₂ |

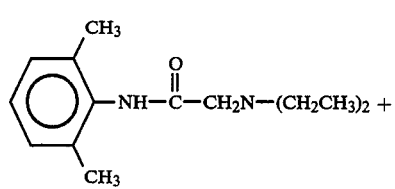

$H_2O \longrightarrow$

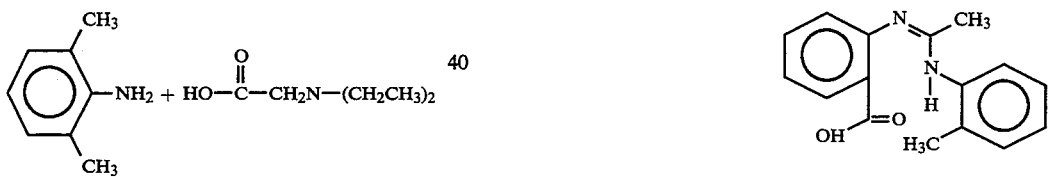

Identity of X, R₁, and R₂ in the hydrolysis of methaqualone:

(methaqualone structure) + H₂O ⟶ (hydrolysis product structure)

TABLE 27

| Substrate (methaqualone) | X | R₁ | R₂ |
|---|---|---|---|
| (methaqualone structure) | -N(CH₃)-C(=O)- acetyl-N-methyl | (2-methylphenyl-N=C(CH₃)-) | (2-methylphenyl, H₃C) |

Identity of Y, R₁', R₂' in a hapten which corresponds to the substrate in the reaction above:

TABLE 25

| Substrate (lidocaine) | X | R₁ | R₂ |
|---|---|---|---|
| (2,6-dimethylphenyl)—NH—C(=O)—CH₂N—(CH₂CH₃)₂ + H₂O | -NH-C(=O)- | (2,6-dimethylphenyl with CH₃) | -CH₂N—(CH₂CH₃)₂ |

TABLE 28

| Hapten | Y | $R_1'$ | $R_2'$ |
|---|---|---|---|

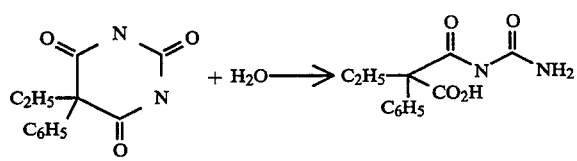

Identity of X, $R_1$, and $R_2$ in the hydrolytic breakdown of phenobarbital:

TABLE 29

| Substrate (phenobarbital) | X | $R_1$ | $R_2$ |
|---|---|---|---|
| | | | $-C_6H_5$ |

Identity of Y, $R_1'$, $R_2'$ in a hapten which corresponds to the substrate in the reaction above:

TABLE 30

| Hapten | Y | $R_1'$ | $R_2'$ |
|---|---|---|---|

Identity of X, $R_1$, and $R_2$ in the hydrolysis of dideoxyadenosine phosphate:

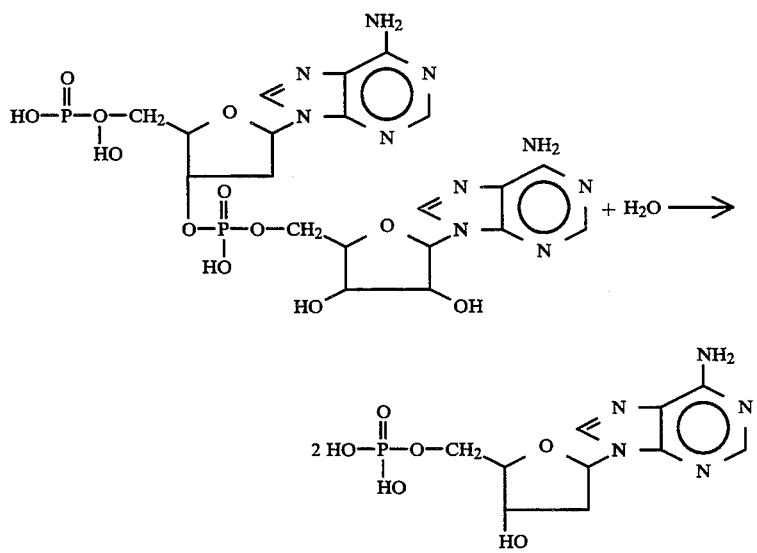

TABLE 31

| Substrate (dideoxyadenosine phosphate) | X |
|---|---|

TABLE 31-continued

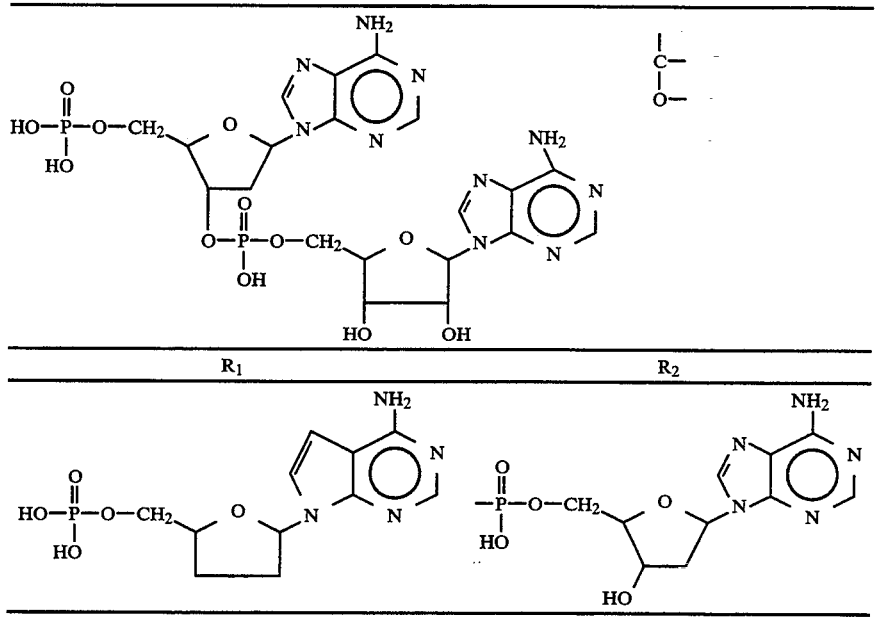

Identity of Y, $R_1'$, $R_2'$ in a hapten which corresponds to the substrate in the reaction above:

TABLE 32

| Hapten | Y |
|---|---|

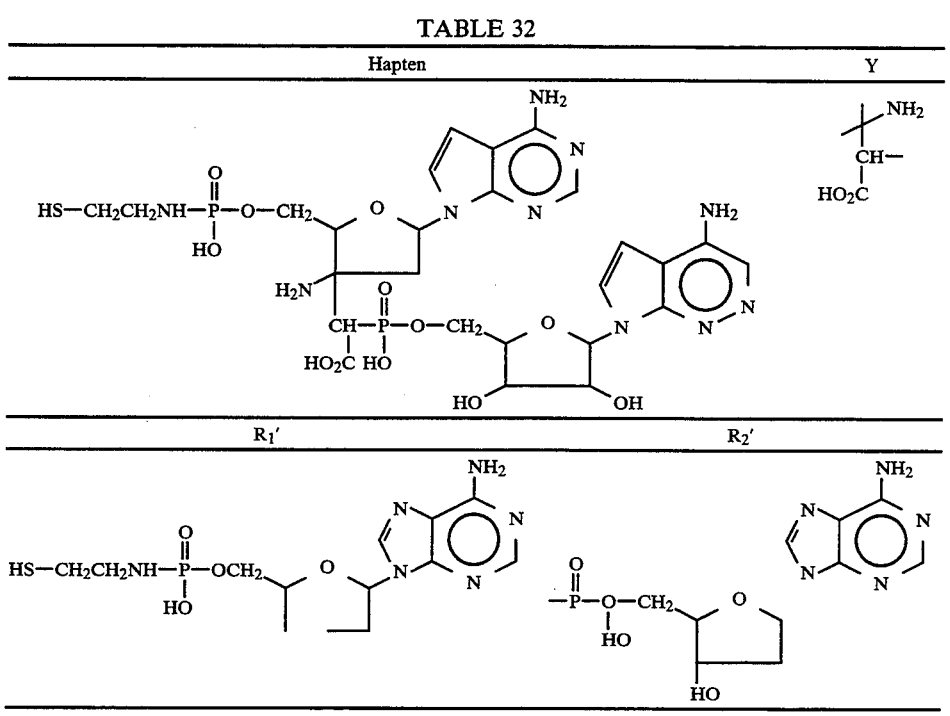

The substituents Q position complementary, catalytic groups within the antibody binding surface and create an additional cavity or cavities capable of enclosing cofactor molecules.

Table 33 presents some exemplary substituents, i.e. Q in the above representation.

TABLE 33

Substituents Q On The Hapten Nuclei Y

A) For introducing a (+) charge(s) in the catalyst antibody
—$CO_2^{(-)}$
—$PO_4^{(-2)}$
—$SO_4^{(-2)}$

TABLE 33-continued

Substituents Q On The Hapten Nuclei Y
—$SO_3^{(-2)}$

B) For introducing a (—) charge(s) in the catalyst antibody
—$NH_3^{(+)}$
—$NRH_2^+$
—$NR_2''H^{(+)}$
—$NR_3^{(+)}$
—$SR_2'''^{(+)}$ R, $R_2''$ and $R_3$ = any stable alkyl or aryl group(s) wherein R, $R_2''$ and $R_3$ need not be identical C) To replace —OH of the substrate
—Cl        —Br
—$CF_3$
=O D) To create polar environments

TABLE 33-continued

Substituents Q On The Hapten Nuclei Y

—NO₂  —Br $\underset{\|}{O}$
—C—NH₂           —CF₃

—N—(C₂F)₂
—Cl
—SH
—OH

*E) To create non-polar environments*

—C—(CH₃)₃    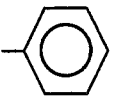

$\underset{\|}{O}$
—C—CH₃       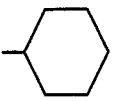

—CH₃
—CH—(CH₃)₂

*F) To provide a cavity for H₂O*

—CO₂⁽⁺⁾
—NH₂/—NH₃⁽⁺⁾
—NO₂

Table 34 specifies some linking groups appropriate to the invention.

TABLE 34

Partial List Of Linkage Groups For Attachment Of Haptens To Carrier Proteins

| Group | Bond To Carrier |
|---|---|
| —(CH₂)ₙ*—NH₂ | amide |
| —CO₂H | ester, amide |
| —OH | ester |
| —SH | disulfide |

ₙ*can be varied to maximize attachment and antigenicity.

Groups other than —CH₂—(C(=O))—CH₂NH— for example) can be used as spacers.

The process of this invention comprises selecting or synthesizing a hapten according to the algorithm set forth above, preferably covalently linking said hapten(s) to carrier species such as keyhole limpet hemocyanin or similar proteins in standard use for this purpose via the linking residues provided for above, and injecting the complex into an appropriate animal as antigen to stimulate the immune response. Following a time sufficient for said response to develop, the animal is bled, serum is extracted and fractionated (preferably over a column containing covalently linked hapten) to remove non-specific antibodies including those responsive to carrier alone, according to standard procedures. This purified IgG fraction is assayed by conventional means for catalytic activity that can be inhibited by the hapten itself, but not by unrelated molecules of comparable size or structure.

Such antibody catalysts, as will be apparent to those of skill in the art, are useful as catalysts for chemical reactions of industrial importance, e.g., as active ingredients in detergents, for degrading carbohydrates in the conversion of starch to sugar, and for cheese production and for treatment of human diseases.

Other areas that antibody catalysts are useful for are in organic synthesis and site specific cleavage of biopolymers. Also the inactivation of drugs or toxins is another useful area.

In organic synthesis they are particularly useful in synthesis of chiral compounds, the selective reaction of one of a number of similar bonds, and catalysis of one of a mixture of compounds. Traditional catalysts tend to lack stereospecificity, selectivity, and/or substrate specificity. Besides overcoming these problems, antibody catalysts offer significant rate enhancements and milder reaction conditions then traditional catalysts.

Antibody catalysts have the advantage that they can be produced for a potentially broader set of reactions then those reactions catalyzed by enzymes. Additionally, many enzymes are unstable. In contrast, antibody catalysts being immunoglobins are stable.

Antibody catalysts also are of considerable use when protective groups are employed in synthesis. An antibody catalyst can remove a protective group without altering the substrate in any other respect.

As site-specific cleavage catalysts, antibody catalysts are useful from protein sequencing to anti-cancer therapy. To facilitate protein sequencing, for example, an antibody catalyst can be produced to catalyze the hydrolysis of N-terminal formyl or acetyl groups, and can be produced to catalyze the cleavage of proteins at the rare amino acid tryptophan.

The following examples are offered by way of illustration and not by way of limitation. The following examples are intended to be prophetic and not intended to be representations of work actually done.

This example illustrates the preparation of an antibody catalyst for the hydrolysis of the substrate uric acid. The synthesis of the hapten is illustrated in steps A-N as follows:

EXAMPLE 1

Synthesis of Uric Acid Hydrolase Hapten

A. n-Butyllithium (100 ml of a 1.55N solution in hexane) is added, with stirring, to 280 ml anhydrous ether at (—)78° containing diisopropylamine (0.155 mole) under a nitrogen atmosphere. 1,1,1-Trifluoroacetone (0.155 mole) is added dropwise over a period of 1 hour. This is followed by the rapid addition, with vigorous stirring, of diethylcarbonate (0.175 mole). The reaction mixture is allowed to come to room temperature and neutralized by the addition of 3.2N HCl with rapid stirring. The neutralized mixtured is poured into 400 ml cold H₂O and the organic layer separated. The aqueous layer is washed with ether (3×50 ml). The organic layers are combined, evaporated to dryness, and the residue resuspended in absolute ethanol. The ethanol is cooled until crystallization occurs. Yield 80%, C₆H₇F₃O₃.

B. The product A (0.50 mole) is added to 500 ml absolute ethanol containing metallic sodium (1.0 mole) with stirring. Then bring the solution to a gentle reflux and add ethyl (1-bromo) acetate (0.55 mole) over a period of two hours. Refluxing is continued until the solution gives a neutral reaction with moist litmus paper (6-10 hours). When refluxing is complete cool, remove the NaBr by filtration, wash the NaBr with 100 ml absolute ethanol, combine the ethanol solutions, and evaporate the ethanol solution to dryness. The residue is dissolved in a minimum amount of ethanol and added to 1 liter of 5% NaOH. This mixture is stirred for 4 hours at room temperature. The mixture is allowed to stand and any organic layer that separates is discarded. One hundred milliters of 3.6M $H_2SO_4$ is slowly added to the aqueous layer. When evolution of $CO_2$ stops, the solution is heated gradually and held there until ⅓–½ of the starting volume has been collected. Sodium hydroxide is added to the distillate until the pH is slightly alkaline. The NaOH treated distillate is redistilled and 80–90% of the starting volume is collected. The ketone product separates from the aqueous layer and is collected. The combined aqueous layers are distilled twice more, as described above, and the ketone fractions pooled. The ketone is added to an equivalent volume of ether, washed with one volume of saturated $CaCl_2$, dried, and crystallized. Yield 50%, $C_5H_5F_3O_3$.

C. Lithium diisopropylamine is prepared as in part A with the substitution of anhydrous tetrahydrofuran (THF) for hexane and ether. The product from B (0.070 mole) in 20 ml anhydrous THF is added dropwise, with stirring, over an hour. After the addition is complete, stirring is continued for 10 minutes and phenylselenium chloride (0.075 mole) in 20 ml anhydrous THF is added rapidly. The mixture is allowed to warm to 0°. Hydrogen peroxide (0.75 mole) is added and the solution is brought to room temperature and stirred for 30 minutes. The organic layers is dried, the solvent removed at reduced pressure, and the residue is taken up in a minimal amount of ether and crystallized by cooling the solution. Yield 70%, $C_5H_3F_3O_3$.

D. The product C (0.10 mole) in 100 ml anhydrous carbon tetrachloride is protected from light and bromine (0.10 mole) is added. The mixture is stirred at 20° for 45 minutes. The solvent and excess bromine are removed under reduced pressure. The residue is dissolved in a minimal amount of ether and cooled to induce crystallization. Yield 55%, $C_5H_3Br_2F_3O_3$.

E. Allyl urea (0.10 mole) is dissolved in 25 ml of anhydrous benzene and the flask flushed with nitrogen. Sodium hydride (0.45 mole) is added to the benzene solution with stirring. When the addition is complete, the mixture is brought to reflux and the production D (0.15 mole) in 20 ml anhydrous benzene is added dropwise. Refluxing is continued for 7 hours after the second addition is completed. The reaction mixture is the cooled and equal volumes of 95% ethanol and water are added sequentially. The benzene layer is separated and washed with 5% aqueous salt and then $H_2O$. The benzene layer is then dried, the benzene evaporated under reduced pressure,and the residue taken up in a minimal volume of chloroform-benzene (3:1 v/v). The solution is spotted and run on a paper chromatography system with a developer of methanol-chloroform-benzene (2:1:0.5 v/v/v). The desired spot is eluted with anhydrous ether and the product crystallized by cooling the solution. Yield 40%, $C_9H_9F_3N_2O_4$.

F. Triethylamine (0.4 mole) in 300 ml acetone is added to product E (0.33 mole) in 225 ml acetone/water (2:1 v/v) at $(-)5°$. The mixture is stirred briefly and ethyl chloroformate (0.4 mole) in 100 ml acetone is added. The resulting solution is stirred at $(-)5°$ for 30 minutes. With screens in place (in case of explosion) 32.5 g sodium azide in 200 ml $H_2O$ is added. The temperature is maintained at $-15°$ to $0°$ and the mixture is stirred for 2 hours. The solution is poured into and equal volume of ice cold, saturated salt solution and then extracted with ether (5×100 ml). The combined ether extracts are dried, an equal volume of absolute ethanol is added. The mixture heated gentle until all the ether had been driven off, and then refluxed for 6 hours. The ethanol is removed under reduced pressure. The residue is dissolved with 300 ml 40% aqueous NaOH and the resulting solution refluxed for 36 hours. The solution is cooled, extracted with ether (10×50 ml), the ether extracts combined, the combined extracts water washed and dried, and the ether evaporated under reduced pressure. The residue is taken up in absolute ethanol and crystallized by cooling the solution. Yield 47%, $C_8H_9F_3N_3O_2$.

G. Diethlymalonate (0.10 mole) is added to 100 ml absolute ethanol containing metallic sodium (0.10 mole) with stirring. The resulting solution is brought to a gentle reflux and ethyl chloroformate (0.11 mole) is added over a period of two hours. Refluxing is continued until the solution gives a neutral reaction with moist litmus paper (10–15 hours). After refluxing, the solution is cooled and the NaCl removed by filtration. The NaCl is washed with 10 ml absolute ethanol, the ethanol fractions combined and dried, and the ethanol evaporated at reduced pressure. Yield 65%, $C_{10}H_{16}O_6$.

H. Produce F (0.01 mole) is dissolved in 100 ml $H_2O$ at 50°. Product G (0.01 mole) is added to the resulting solution and the mixture stirred for 10 hours at 50°. The temperature is then reduced to 5° and the solution adjusted to pH 14 with 6N NaOH. The resulting mixture is held at 5° and stirred for 6 hours. The pH is then adjusted to 7 with 6N HCl after the mixture has been allowed to come to room temperature. The precipitated product is collected by filtration. The filtrate is washed with 20 ml cold $H_2O$ and 20 ml cold ethanol and then dried under reduced pressure. The resulting solid is dissolved in glycerol and recrystallized by cooling the solution. Yield 30%, $C_{13}H_{16}F_3N_3O_5$.

I. Product H (0.10 mole) is dissolved in 200 ml 1,1-dichloroethane. Cyclopentadienyliron dicarbonyl tetrafluoroborate (0.11 mole) is added to the resulting solution with stirring. The mixture is brought to reflux and refluxing is continued for 15 minutes. The reaction mixture is then cooled to room temperature and the product is precipitated by the addition of an equal volume of anhydrous ether. The product is collected by filtration and washed with ether. Yield 95%, $C_{20}H_{21}F_7BF_eN_3O_7$.

J. To carbon tetrabromide (0.11 mole) and triphenylphosphine (0.11 mole) in 150 acetonitrile-ether (1:2 v/v) at 25° add product I (0.10 mole). After stirring for 3 hours, an equal volume n-pentane is added to precipitate the triphenylphosphine oxide which is formed. The solution is filtered to remove the precipitate, the solvent evaporated under reduced pressure, and the residue recrystallized from n-pentane. Yield 90%—$C_{20}H_{20}F_7BBrFeN_3O_6$.

K. Product J (0.21 mole) is dissolved in 260 ml of toluene containing potassium phthalimide (0.21 mole). The stirred mixture is maintained at 100° for 10 hours. The mixture is then filtered an the filtrate washed with toluene. The toluene fractions are combined and the toluene evaporated under reduced pressure. The residue (78 g) is redissolved in 500 ml of absolute ethanol. The solution is brought to reflux and hydrazine (0.25 mole) is added. Refluxing is continued for 1 hour. The mixture is then cooled, acidified (slightly by the addition of 6N HCl, refluxed an addition 30 minutes, cooled and filtered. The filtrate is washed with absolute ethanol, the ethanol fractions combined and evaporated to dryness under reduced pressure. The residue is resuspended in absolute ethanol containing KOH (0.25 mole), the solution filtered and the ethanol removed under reduced pressure. The residue is dissolved in a minimal amount of chloroform and cooled until crystallization occurs. Yield 49%, $C_{20}H_{23}F_3FeN_4O_7$.

L. Product K (0.05 mole) is dissolved in a minimal amount of anhydrous acetone. Sodium iodide (0.10 mole) is added and the mixture stirred for 30 minutes. The solution is filtered and an equal volume of cold ether is added to precipitate to product. The precipitate is collected by filtration and washed with ether (3×10 ml). Yield 90%, $C_3H_{17}N_4O_4F_3$.

M. The product L (0.10 mole) is dissolved in 100 ml of hot 6N HBr. The flask is flushed with nitrogen and heated to 100° for 1 hour. The mixture is then cooled and neutralized with 6N NaOH. The precipitated product is collected by filtration. The filtrate is redissolved in chloroform and crystallized induced by cooling the solution. Yield $C_{11}H_{14}F_3N_4O_4Br$.

N. The product M (0.20 mole) is added to a stirred mixture of thiourea (0.22 mole) in 25 ml triethylene glycol at 75°. The mixture is stirred until homogeneous and the temperature kept below 130°. After stirring an additional 15 minutes, the pressure is reduced and tetramethylene pentamine (0.10 mole) is added cautiously. The mixture is refluxed until a constant head temperature is reached. Distillation is then begun and the product collected. The distillate is cooled, and equal volume of chloroform is added, and cooling is continued until crystallization occurs. Yield 60%, $C_{11}H_{15}F_3N_4O_4S$.

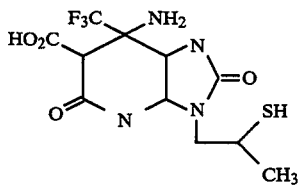

The hapten prepared as above can be used to stimulate an immune response by covalently linking said hapten to a carrier species and isolating antibodies from said immune response which are catalytically active for the hydrolysis of the substrate uric acid.

This example illustrates the preparation of an antibody catalyst for decarboxylation reaction. The substrate in the decarboxylation reaction is prepared in Example 3. The synthesis of the haptens are illustrated in steps A–H as follows:

EXAMPLE 2

Snythesis of Decarboxylation Haptens

A. Diethyl-(2,3-dimethyl)-succinate (0.10 mole) is added to 200 ml tetralin containing $P_2S_3$ (0.20 mole). The resulting mixture is refluxed until a constant head temperature is reached and then distillation of the product is begun. When all of the product had been collected it is cooled, diluted with an equal volume of ether, and crystallized by further cooling. Yield 35%—$C_6H_9S$.

B. A cold mixture of ethyl chloride (0.10 mole) in 30 ml anhydrous ether is added dropwise, over a period of 1 hour, to a stirred mixture of sodium amalgam sand (0.20 mole Na and 0.006 mole Hg) and 0.15 mole 3,4-dimethylthiophene (product A) in 20 ml anhydrous ether at 0°–5°. Upon completion of the addition, the ice bath is removed, the mixture is held below reflux for 1 hour, and then refluxed for 15 minutes. After cooling to 0°–9°, 10 ml anhydrous ether containing 0.10 mole ethylene oxide is added dropwise, with stirring, over an hour. The temperature is then allowed to rise to room temperature and 15 ml absolute ethanol is added. Then 67 ml 3N HCl is added over a period of 30 minutes. The ether layer is separated, dried, and evaporated under reduced pressure to give the product. Yield 50%, $C_8H_{12}OS$.

C. n-Butyllithium, (100 ml of a 1.55N solution in hexane) is added, with stirring, to 280 ml anhydrous ether, at $(-)78°$ containing 0.155 mole diisopropylamine, under a nitrogen atmosphere. Product B (0.0775 mole) is dissolved in a minimum of anhydrous éther and is added dropwise over a period of one hour. This is followed by the rapid addition, with vigorous stirring of either: 1) methyl acetate (0.0775 mole), 2) acetamide (0.0775 mole), or 3) methyl-chlorophosphinamide (0.0775 mole). The reaction mixture is allowed to come to room temperature and neutralized by pouring into 25 ml 3.2N HCl. Four hundred ml $H_2O$ is added, the organic layer separated, and the aqueous layer is extracted with dichloromethane. The combined organic layers are then dried, the solvent evaporated under reduced pressure, and the residue distilled under vacuum. The distillate is cooled, and equal volume of anhydrous ether added, and cooling continued until crystallization occurs: Yield 1–10%, $C_{12}H_{18}O_4S$ 2–15%, $C_{11}H_{17}NO_3S$ 3–8%, $C_9H_{16}NO_2PS$ D. Acetyl chloride (0.10 mole) is added dropwise to 100 ml of petroleum ether containing $AlCl_3$ (0.11 mole) and product B (0.10 mole) with continuous stirring. The mixture is held at 30°–40° for 1 hour, cooled, and washed with saturated sodium bicarbonate, saturated salt, and water. The aqueous washes are extracted with ether. The ether washes are combined with the petroleum ether solution, dried, the solvent removed at reduced pressure, and the residue resuspended in ether. The ether is cooled until crystallization occurs. Yield 65%, $C_{10}H_{14}O_2S$.

E. Product D (0.30 mole) in 50 ml ether is added to 50 ml $H_2O$, at 5°–10°, containing ammonium chloride (0.37 mole) with vigorous stirring. To this mixture sodium cyanide (0.32 mole) in 35 ml $H_2O$ is slowly added. Stirring is continued and the temperature is maintained at 5°–10°. The mixture is stirred for 1 hour after cyanide addition is complete and then allowed to stand overnight. The ether layer is separated and the aqueous layer washed (6×30 ml ether). The combined ether layers are dried, the solvent evaporated under reduced pressure and the residue crystallized from an ether extract of said residue. Yield 75%, $C_{11}H_{15}NO_2S$.

F. Pulverized quaternary n-butylphosphonium iodide (0.02 mole) is covered with 100 ml anhydrous ether and the flask maintained under a nitrogen atmosphere. n-Butyllithium (0.02 mole) in 20 ml anhydrous ether is added dropwise to the stirred suspension over a 1 hour period. The mixture is refluxed until a clear orange-red solution forms, a small amount of additional n-butylphosphonium iodide is added, and refluxing continued for 1 hour. The product E (0.02 mole), in 50 ml anhydrous ether is added dropwise with vigorous stirring, over a 1 hour period. This mixture is refluxed until most of the color fades (2–48 hours), and the solvent evaporated under reduced pressure. The residue is dissolved in 60 ml methanol-water-conc.HCl (1:1:1 by volume) and refluxed for two hours. The resulting mixture is steam distilled until the product ketone is no longer detected in the distillate. The distillate is cooled, an equal volume of anhydrous ether is added,and cooling continued until crystallization occurs. Yield 60%, $C_{12}H_{18}O_3S$.

G. The product C1,C2,C3, or F (0.01 mole) is added to 20 ml anhydrous pyridine. p-Toluenesulfonate(tosyl) chloride (0.01 mole) is slowly added to the stirred mixture. After the addition is complete, the mixture is stirred for 1 hour. The resulting mixture is poured into 150 ml ice water, the precipitate collected and washed (3×10 ml) with ice water. The precipitate is recrystallized from ethanol. Yield 95%—

1: $C_{19}H_{24}O_6S_2$
2: $C_{18}H_{23}NO_5S_2$
3: $C_{16}H_{22}NO_4PS_2$
4: $C_{19}H_{24}O_5S_2$

H. The product of G (0.20 mole)—G1, G2, G3, or G4—is added to a stirred mixture of thiourea (0.22 mole) in 25 ml triethylene glycol at 75°. The mixture is stirred until homogeneous and kept below 130°. After stirring an additional 15 minutes, the pressure is reduced and tetramethylenepentamine (0.10 mole) is added cautiously. The mixture is refluxed until a constant head temperature is reached when distillation is begun to collect the product. The distillate is cooled, an equal volume of ether is added, and cooling continued until crystallization occurs.
Yield 70%,
1. $C_{12}H_{18}O_4S_2$
2. $C_{11}H_{17}NO_3S_2$
3. $C_9H_{16}NO_2PS_2$
4. $C_{12}H_{18}O_3S_2$ 1:
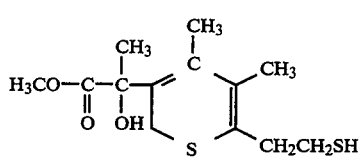

2:
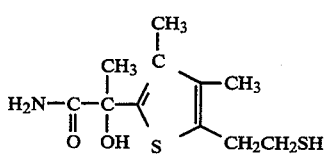

3:
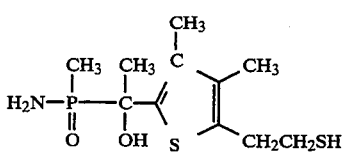

4:
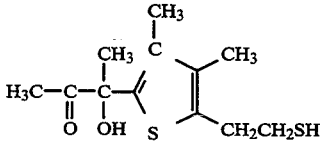

The haptens prepared as above can be used to stimulate an immune response by covalently linking said haptens to a carrier species and isolating antibodies from said immune response which are catalytically active for the decarboxylation reaction of the substrate prepared in Example 3.

EXAMPLE 3

Snythesis of the Decarboxylation Substrate

A. Thiamine ($C_{12}H_{17}N_4OS$) [0.038 mole] is mixed with 150 ml of 2.6N sodium sulfite solution which had been adjusted to pH 4.8–5.0 with sulfurous acid. This mixture is heated on a steam bath for 1 hour. The precipitate is removed by filtration and washed (3×15 ml $H_2O$ pH 5.0). The washings are combined with the mother liquor and brought to pH 10 with 6N NaOH. The resulting solution is extracted with chloroform (5×100 ml). The combined chloroform extracts are in turn extracted with 0.1N HCl. The combined acid extracts are evaporated at reduced pressure. The residue is resuspended in a minimal amount of absolute ethanol, the ethanol removed under vacuum, and the resulting residue is recrystallized from a minimal amount of absolute ethanol by the addition of dioxane. Yield —97%-, $C_6H_9NSO$.

B. n-Butyllithium (213 ml of a 1.55N solution in hexane) is added, with stirring, to 280 ml anhydrous ether at $^{(-)}78°$ under a nitrogen atmosphere. Next 0.33 mole of product A is added dropwise over a period of 45 minutes, with stirring. This is followed by 0.33 mole of ethyl pyruvate, added as rapidly as possible with vigorous stirring. The resulting mixture is allowed to come to room temperature and then is neutralized by pouring into 103 ml 3.2N ethanolic HCl. Three hundred ml of $H_2O$ is added to the neutralized mixture and the organic layer allowed to separate. The organic layer is removed and the aqueous layer is extracted with dichloromethane. The combined organic layers are then dried, evaporated at reduced pressure, and distilled under high vacuum to yield a fraction containing the product. This fraction is diluted with an equal volume of ether and cooled until crystallization occurs. The crystals are collected by filtration and washed (3×5 ml) with cold ether. Yield 10%, $C_{11}H_{17}NO_3S$.

C. The product of B (1.06 g) dissolved in a minimum of nitromethane is added to trimethyloxonium tetrafluroborate (0.618 g) also dissolved in a minimum of nitromethane. After completion of the exothermic reaction, the mixture is allowed to stand for one hour at room temperature. The mixture is then evaporated to dryness at reduced pressure, the residue washed with anhydrous ether, covered with a layer of n-pentane and cooled and agitated until solidification occurs. Filtration yields the desired product. Yield 80%, $C_{12}H_{20}BF_4NO_3S$.

D. The product of C (0.001 mole) is dissolved in 2.5 ml $H_2O$ and applied to an ion exchange column (BioRad Ag 1-X8, 50–100 mesh, $Cl^{(-)}$form—3.6 ml, 5 meg.). The sample is eluted with 40 ml $H_2O$. The eluate is evaporated under reduced pressure to give the chloride salt of C. Yield 67%, $C_{12}H_{20}ClNO_3S$.

E. The product of D (0.01 mole) is added to 20 ml of anhydrous pyridine. Then 0.01 mole trityl chloride is added to the mixture and the resulting mixture is heated with a boiling water bath for 2 hours. The mixture is then poured into ice water, the filtrate collected, and washed with ice water (3×10 ml). Yield 80%, $C_{31}H_{34}ClNO_3S$.

F. The product of E (0.10) mole) is added to 50 ml of anhydrous ether containing anhydrous N,N-dimethylanaline (0.10 mole). Then 0.10 mole acetyl chloride is added, with stirring, at a rate fast enough to keep the ether refluxing. Upon completion of the aetyl chloride addition, reflux for 2 hours and allow to stand for 4 hours. Separate the solid N,N-dimethylanaline HCl by filtration and wash with ether (3×5 ml). Combine the washings with the mother liquor, wash with cold 3.2N HCl until the acid extract does not cloud upon alkalinization, dry, remove ether at reduced pressure, and distill desired fraction under vacuum. The collected fraction is cooled and recrystallized from ethanol. Yield 75%, $C_{14}H_{22}NO_5ClS$.

G. To 0.11 mole carbon tetrabromide and 0.11 mole triphenyl phospine in 100 ml of acetonitrile at 25° add 0.10 mole of product F dissolved in a minimum of acetonitrile. After 3 hours, n-pentane is added to precipitate the resulting triphenylphosphine oxide. The acetonitrile is removed under reduced pressure and the resulting residue taken up in a minimum amount of ether and crystallized by cooling. Yield 80%, $C_{14}H_{21}BrClNO_4S$.

H. The product from G (0.2 mole) is added to a stirred mixture of 0.22 mole thiourea in 25 ml triethylene glycol at 75°. The mixture is stirred until homogeneous and kept below 130°. After stirring an additional 15 minutes, the pressure is reduced and 0.1 mole tetramethylenepentamine is added cautiously. The mixture is refluxed until a constant head temperature is reached when distillation to collect the product is begun. Yield 70%—$C_{14}H_{22}ClNO_4S_2$.

I. The product of H (0.15 mole) is dissolved in 60 ml 37% HCl and held at 83° for 18 minutes. The solution is then cooled and evaporated to dryness under reduced pressure. The residue is redissolved in a minimal amount of 3N HCl and precipitated by the addition of 3 volumes of ether. The final product is collected by filtration. Yield 35%, $C_{10}H_{16}NO_3S_2Cl$-I.

Or if the alcohol is to be used as the substrate the product is used in reaction Step I to yield $C_{10}H_{16}NO_4SCl$-II.

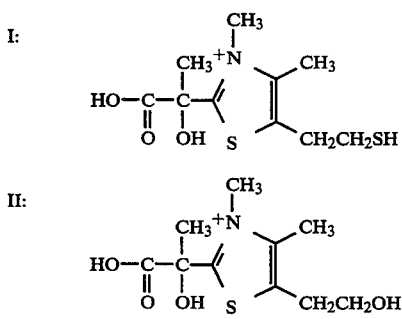

This example illustrates the preparation of an antibody catalyst for a heterolytic fragmentation reaction. The substrate in the heterolytic fragmentation reaction is prepared in Example 5. The synthesis of the hapten is illustrated in steps A–J.

EXAMPLE 4

Synthesis of Heterolytic Fragmentation Hapten

A. A solution of 2-methyl propene (0.15 mole) in THF containing lithium diisopropylamine (0.155 mole) is prepared as described in part A, Heterolytic Fragmentation Substrate Synthesis. 2-Bromoethane disulfuide (0.075 mole) is added to this mixture as rapidly as possible with vigorous stirring. The resulting solution is allowed to come to room temperature and is neutralized by the addition of 20 ml 3.2N HCl with rapid stirring. Four hundred ml of $H_2O$ is added, the organic layer separated, and the aqueous layer extracted with dichloromethane. The organic layers are combined, dried, and the solvent removed under reduced pressure. The residue is redissolved using a minimal amount of chloroform and the solution cooled until crystallization occurs. Yield 65%, $C_{12}H_{22}S_2$.

B. The product A (0.05 mole) is redissolved in 150 ml chloroform. m-Chloroperbenzoic acid (0.06 mole) is added to this solution and the resulting mixture stirred at room temperature until a negative starch paper test is given (2–5 hours). Chloroform is added, as needed, to dissolve any precipitate which may form. The solution is then washed with 10% aqueous sodium bicarbonate and then with water. The organic layer is dried and the solvent evaporated at reduced pressure. The residue is recrystallized from chloroform. Yield 70% $C_{12}H_{22}O_2S_2$.

C. The product B (0.01 mole) is dissolved in 50 ml acetone—water (1:1 v/v) containing sodium hydroxide (0.001 mole). This mixture is brought to 40° and stirred for 3 hours. An equal volume of ether is added, after cooling, and the mixture is shaken. The organic layer is allowed to separate and is washed with water (3×10 ml). The organic layer is then dried and the solvent removed by evaporation under reduced pressure. The residue is redissolved in a minimal amount of ether and cooled until crystallization occurs. Yield 90%, $C_{12}H_{26}O_4S_2$.

D. An oxidizer is prepared by adding chromium trioxide (0.013 mole), hydrogen chloride (0.013 mole), and powdered sodium acetate (0.01 mole) to 150 ml of dichbromethane containing pyridine (0.013 mole). This mixture is stirred for 15 minutes, brought to 25°, and product C dissolved in a minimal amount of dichloroethane is added. The temperature is held at 25° and the mixture stirred for 1 hour. Two hundred milliliters of water is added, the mixture shaken, and the organic layer allowed to separate. The organic layer is washed with saturated sodium bicarbonate, water, and then dried. The solvent is removed under reduced pressure and the residue recrystallized from anhydrous ether. Yield 95% $C_{12}H_{22}O_4S_2$.

E. Product D (0.02 mole) is added to 150 ml absolute ethanol containing ethyl-triphenyl phosphine bromide. Five hundred milliliters of absolute ethanol, 1.4M in potassium ethoxide, is added to the stirred solution. The resulting mixture is allowed to stand for 30 minutes at room temperature and is then refluxed for 2 hours. After refluxing, the solution is concentrated to 100 ml. 300 ml $H_2O$ is added, and the solution stirred for 10 minutes. The solution is then extracted with ether (3×100 ml), the combined ether fraction dried and evaporated under reduced pressure, and the residue recrystallized from chloroform. Yield 80%, $C_{16}H_{30}O_2S_2$.

F. Product E (0.05 mole) is added to dicyclohexylborane (0.05 mole) in 5 ml anhydrous THF under a nitrogen atmosphere. The mixture is stirred for one hour at 25°. The temperature is then reduced to 0° and the flask shielded from light. Bromine (0.05 mole), in 20 ml anhydrous THF at 0°, is added and the resulting mixture is stirred for 30 minutes at 0°. Ten milliliters of water is added; followed by 30 ml of ether. The organic layer is separated and washed with water (2×15 ml). The organic layer is then dried and the solvent evaporated under reduced pressure. The residue is crystallized from ether. Yield 65%, $C_{16}H_{32}Br_2O_2S_2$.

G. Product F (0.21 mole) is dissolved in 260 ml of toluene containing potassium phthalimide (0.21 mole). The stirred mixture is maintained at 100° for 10 hours. The mixture is cooled, filtered, and the filtrate washed with toluene. The combined toluene fractions are evaporated under reduced pressure. The residue (66 g) is redissolved in 500 ml of absolute ethanol. The solution is brought to reflux and hydrazine (0.25 mole) is added.

Refluxing is continued for 1 hour. The mixture is cooled, acidified (slightly) by the addition of 6N HCl, refluxed an additional 30 minutes, cooled again, and filtered. The filtrate is washed with absolute ethanol, the ethanol containing KOH (0.25 mole), the solution filtered, and the ethanol evaporated under reduced pressure. The residue is crystallized from ether. Yield 49%, $C_{16}H_{36}N_2O_2S_2$.

H. Product G (0.10 mole) is added to 150 ml acetonitrile-ether (1:2 v/v) containing carbontetrabromide (0.11 mole) and triphenylphosphine (0.11 mole) at 25°. After stirring for 3 hours, an equal volume of n-pentane is added and the precipitated triphenylphosphine oxide removed by filtration. The solvent is evaporated under reduced pressure and the residue crystallized from ether. The crystals are redissolved in 95% ethanol and sodium cyanide (0.12 mole) is added. The mixture is refluxed for 5 hours. After refluxing, the mixture is cooled, filtered, 100 ml of $H_2O$ is added, 100 ml ether is added, the mixture is shaken and the organic layer allowed to separate. The aqueous layer is washed with ether. The combined ether layers are evaporated under reduced pressure and the residue crystallized from chloroform. Yield 40%, $C_{18}H_{34}N_4S_2$.

I. Product G (0.17 mole) is dissolved in 140 ml ethyleneglycol monoethyl ether. Potassium hydroxide (0.60 mole) in 16 ml $H_2O$ is added and the mixture refluxed with nitrogen bubbling through the solution. Refluxing is continued until the effluent gas will not neutralize 1 ml of 0.1 NHCl in 5 minutes (about 6 hours). The reaction mixture is then cooled and poured into 60 ml conc. HCl. The resulting mixture is washed with ether (5×50 ml), the combined ether layers washed with 10% aqueous sodium bicarbonate and water, dried, and the either evaporated under reduced pressure. The residue is crystallized from chloroform. Yield 77%, $C_{18}H_{36}N_2O_4S_2$.

J. The product of I (0.02 mole) and triphenyl phosphine (0.021 mole) are dissolved in 75 ml dioxane—$H_2O$ (4:1 v/v) containing two drops conc.—HCl. This mixture, under a nitrogen atmosphere, is brought to 40° and stirred for 30 minutes. The solvent is removed under reduced pressure and the product resuspended in anhydrous ether. The solution is washed (3×10 ml) with water, dried, and the ether removed under reduced pressure. The residue is crystallized from chloroform. Yield 60%, $C_9H_{19}NO_2S$.

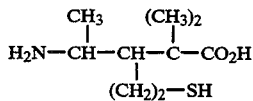

The hapten prepared as above can be used to stimulate an immune response by covalently linking said hapten to a carrier species and isolating antibodies from said immune response which are catalytically active for the heterolytic fragmentation reaction of the substrate prepared in Example 5.

EXAMPLE 5

Synthesis of Heterolytic Fragmentation Substrate

A. n-Butyllithium (100 ml of 1.55N solution in hexane) is added, with stirring, to 280 ml anhydrous tetrahydrofuran (THF), at (−) 78°, containing diisopropylamine (0.155 mole) under a nitrogen atmosphere. Anhydrous 2-methyl propene is bubbled into this solution until 0.15 moles have been dissolved. This is followed by the rapid addition of acetaldehyde (0.15 moles) with vigorous stirring. The reaction mixture is allowed to come to room temperature and neutralized by the addition of 20 ml of 3.2N HCl. Four hundred ml of $H_2O$ is added, the organic layer separated, and the aqueous layer extracted with dichloromethane. The combined organic layers are dried, the solvent removed under reduced pressure, and the residue redissolved in a minimal amount of ether. The product is crystallized by cooling the ether solution. Yield 75%, $C_6H_{12}O$.

B. Product A (0.07 mole) dissolved in a minimum of anhydrous THF is added dropwise, with stirring, to a solution of lithium drisoproylamine at (−) 78° (as prepared above). 2-Bromoethane disulfide (0.035 mole) is added to the mixture as rapidly as possible with vigorous stirring. The resulting solution is allowed to come to room temperature and is neutralized by the addition of 50 ml 3.2 NHCl with rapid stirring. Four hundred ml of $H_2O$ is added, the organic layer separated, and the aqueous layer extracted with dichloromethane. The combined organic layers are dried, the solvent is removed under reduced pressure, and the residue redissolved in a minimal amount of benzene. The product is crystallized by cooling the benzene solution. Yield 60%, $C_{16}H_{30}O_2S_2$.

C. Product B. (0.05 mole) is added to dicyclohexylborane (0.05 mole) in 5 ml anhydrous THF under a nitrogen atmosphere. The mixture is stirred for 1 hour at 25°. The temperature is then reduced to 0° and the flask shielded from light. Bromine (0.05 mole), in 20 ml anhydrous THF at 0°, is added to the solution and the resulting mixture stirred for 30 minutes at 0°. Ten milliliters of water is added; followed by 30 ml ether. The organic layer is separated and washed with $H_2O$ (2×15 ml). The organic layer is then dried and the solvent evaporated under reduced pressure. The residue is redissolved in acetone and crystallized by cooling the solution. Yield 65%, $C_{16}H_{32}Br_2O_2S_2$.

D. The product C (0.02 mole) and triphenyl phosphine (0.021 mole) are dissolved in 75 ml diotane—$H_2O$ (4:1 v/v) containing 2 drops conc.—HCl. This mixture is brought to 40° under a nitrogen atmosphere and stirred for 30 minutes. The solvent is removed under reduced pressure and the desired product redissolved in 50 ml anhydrous ether. The solution is washed with $H_2O$ (3×10 ml), dried, and the ether evaporated under reduced pressure. The residue is taken up in a minimal amount of chloroform and cooled until crystallization occurs. Yield 60%, $C_8H_{17}BrOS$.

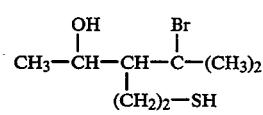

It is the intent of the inventors to commercially develop the antibody catalysts described and claimed herein under the trademark Immunozyme.

What is claimed is:

1. A method for catalyzing a chemical reaction wherein a reactant is converted to a product comprising contacting said reactant with at least one antibody catalyst, said antibody catalyst having been produced by a method comprising the steps of:

(a) identifying a reactant represented by formula $R_1—X—R_2$ for said chemical reaction;
  (b) selecting a hapten which shares common antigenic determinants with said reactant and wherein said hapten is structurally and chemically different from said reactant in the vicinity of the reaction site, said hapten represented by formula

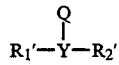

wherein X is a portion of the reactant molecule altered by the chemical reaction and which comprises one or more nuclei and associated bonds, said nuclei comprising O, S, N, or C; and wherein Y is a portion of the hapten molecule where Y is related to X such that Y has a higher valence state and one or more additional bonds than X, and which comprises one or more nuclei and associated bonds, said nuclei comprising N, C, or P; and wherein Q represents one or more substituents selected from the group consisting of (a) positively charged substituents, when the catalyst is to have a negatively charged active surface, (b) negatively charged substituents, when the catalyst is to have a positively charged active surface, (c) polar substituents, when the catalyst is to have a polar active surface, (d) non-polar substituents, when the catalyst is to have a non-polar active surface, and (e) substituents of substantial bulk, when the catalyst is to have a cavity, and wherein Q can contain a group capable of linking the hapten to a carrier and wherein $R_1$, $R_2$, $R_1'$ and $R_2'$ represent the residual chemical groups of the reactant and hapten which do not participate in the catalytic events, and $R_1$ and $R_1'$, and $R_2$ and $R_2'$ are, respectively, substantially similar to each other, said $R_1'$ and $R_2'$ being of similar size and charge to $R_1$ and $R_2$, respectively;
  (c) stimulating an immune response by said hapten; and
  (d) isolating antibodies resulting from said immune response which antibodies are catalytically active for said chemical reaction.

2. A method as recited in claim 1 wherein X is O or S and Y is N or C.

3. A method as recited in claim 1 wherein X is N and Y is C.

4. A method as recited in claim 1 wherein X is C and Y is P.

5. A method as recited in claim 1 wherein Q is a positively charged substituent.

6. A method as recited in claim 5 wherein Q is a substituent selected from the group consisting of $-NH_3^{(+)}$, $-NRH_2^{(+)}$, $-NR_2''H^{(+)}$, $-NR_3^{(+)}$ and $-SR_2'''^{(+)}$, wherein R, $R_2''$ and $R_3$ are, independently from one another, any stable alkyl or aryl group(s).

7. A method as recited in claim 1 wherein Q is a negatively charged substituent.

8. A method as recited in claim 7 wherein Q is a substituent selected from the group consisting of $-CO_2^{(-)}$, $-PO_4^{(-2)}$, $SO_4^{(-2)}$ and $-SO_3^{(-2)}$.

9. A method as recited in claim 1 wherein Q is a polar substituent.

10. A method as recited in claim 9 wherein Q is a substituent selected from the group consisting of $-NO_2$, $-C(=O)-NH_2$, $-N-(CH_2F)_2$, $-Cl$, $-SH$, $-OH$, $-Br$, and $-CF_3$.

11. A method as recited in claim 1 wherein Q is a non-polar substituent.

12. A method as recited in claim 11 wherein Q is a substituent selected from the group consisting of

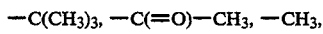

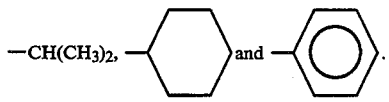

13. A method as recited in claim 1 wherein Q is a substituent of substantial bulk.

14. A method as recited in claim 13 wherein Q is a substituent selected from the group consisting of $-CO_2^{(-)}$, $-NH_2$, $-NH_3^{(+)}$ and $-NO_2$.

15. A method as recited in claim 1 wherein the catalytic antibodies resulting from the immune response are derived monoclonally.

16. A method as recited in claim 1 wherein the catalytic antibodies resulting from the immune response are derived polyclonally.

17. A method as recited in claim 1 wherein the chemical reaction is a general acid-base catalysis reaction.

18. A method as recited in claim 1 wherein the chemical reaction involves charge stabilization or destabilization in the transition state.

19. A method as recited in claim 18 wherein the charge stabilization or destabilization in the transition state is a fragmentation reaction.

20. A method as recited in claim 19 wherein the fragmentation reaction is a decarboxylation reaction.

21. A method as recited in claim 17 wherein the general acid-base catalysis reaction is hydrolysis of uric acid.

22. A method as recited in claim 17 wherein the general acid-base catalysis reaction is hydrolysis of protein molecules comprising a specified sequence of amino acids.

23. A method as recited in claim 17 wherein the general acid-base catalysis reaction is hydrolysis of polydeoxynucleotides or polyribonucleotides comprising a specific sequence.

24. A method as recited in claim 1 wherein the antibody catalyst is purified from a resulting globulin fraction antibody active as a specific catalyst for the chemical reaction.

* * * * *